(12) United States Patent
Rosencwaig

(10) Patent No.: US 7,286,243 B2
(45) Date of Patent: Oct. 23, 2007

(54) BEAM PROFILE COMPLEX REFLECTANCE SYSTEM AND METHOD FOR THIN FILM AND CRITICAL DIMENSION MEASUREMENTS

(75) Inventor: Allan Rosencwaig, Danville, CA (US)

(73) Assignee: Arist Instruments, Inc., Fremont, CA (US)

( * ) Notice: Subject to any disclaimer, the term of this patent is extended or adjusted under 35 U.S.C. 154(b) by 0 days.

(21) Appl. No.: 11/109,525

(22) Filed: Apr. 18, 2005

(65) Prior Publication Data

US 2005/0248773 A1 Nov. 10, 2005

Related U.S. Application Data

(60) Provisional application No. 60/650,937, filed on Feb. 7, 2005, provisional application No. 60/640,182, filed on Dec. 27, 2004, provisional application No. 60/624,865, filed on Nov. 1, 2004, provisional application No. 60/613,040, filed on Sep. 25, 2004, provisional application No. 60/610,896, filed on Sep. 17, 2004, provisional application No. 60/568,215, filed on May 3, 2004, provisional application No. 60/563,725, filed on Apr. 19, 2004.

(51) Int. Cl.
*G01B 11/02* (2006.01)
*G01N 21/41* (2006.01)
*G01J 4/00* (2006.01)

(52) U.S. Cl. ............... 356/504; 356/517; 356/369

(58) Field of Classification Search ............... 356/485, 356/492, 503, 504, 517, 369
See application file for complete search history.

(56) References Cited

U.S. PATENT DOCUMENTS

| | | | |
|---|---|---|---|
| 3,824,017 A | 7/1974 | Galyon | |
| 4,293,224 A | 10/1981 | Gaston et al. | |
| 4,555,766 A | 11/1985 | Wright | |
| 4,999,014 A | 3/1991 | Gold et al. | |
| 5,042,951 A | 8/1991 | Gold et al. | |
| 5,076,696 A * | 12/1991 | Cohn et al. | 356/369 |
| 5,166,752 A | 11/1992 | Spanier et al. | |
| 5,181,080 A | 1/1993 | Fanton et al. | |
| 5,412,473 A | 5/1995 | Rosenwaig et al. | |
| 5,596,411 A | 1/1997 | Fanton et al. | |
| 5,739,909 A | 4/1998 | Blayo et al. | |
| 5,867,276 A | 2/1999 | McNeil et al. | |
| 5,877,859 A | 3/1999 | Aspnes et al. | |
| 5,963,329 A | 10/1999 | Conrad et al. | |
| 6,278,519 B1 | 8/2001 | Rosencwaig et al. | |

(Continued)

*Primary Examiner*—Patrick Connolly
(74) *Attorney, Agent, or Firm*—DLA Piper US LLP

(57) ABSTRACT

Device and method for measuring complex reflectance using a light source for generating a light beam with known polarization state, a lens for focusing the beam onto a sample surface such that various rays within the focused beam create a spread of angles of incidence θ, a waveplate for retarding one polarization state of the beam, a polarizer for generating interference between beam polarization states, and a detector with a two dimensional array of detector elements for generating intensity signals in response to the beam, wherein each detector element corresponds to a unique angle of incidence θ and azimuthal angle φ of the reflected beam. A processor calculates magnitude and phase values for the reflected beam by using the intensity signals corresponding to at least one incident angle θ and a plurality of azimuthal angles φ within the at least one incident angle θ sufficient to enable a meaningful Fourier analysis thereof.

61 Claims, 1 Drawing Sheet

U.S. PATENT DOCUMENTS

| | | |
|---|---|---|
| 6,654,131 B2 | 11/2003 | Opsal et al. |
| 6,678,046 B2 | 1/2004 | Opsal |
| 6,813,034 B2 | 11/2004 | Rosencwaig et al. |
| 6,829,057 B2 | 12/2004 | Opsal et al. |
| 6,836,328 B2 | 12/2004 | Opsal |
| 6,842,259 B2 | 1/2005 | Rosencwaig et al. |
| 6,853,455 B1* | 2/2005 | Dixon et al. .................. 356/491 |
| 2006/0158657 A1* | 7/2006 | De Lega et al. ............. 356/497 |
| 2006/0158658 A1* | 7/2006 | Colonna De Lega et al. .......................... 356/497 |
| 2006/0158659 A1* | 7/2006 | Colonna De Lega et al. .......................... 356/497 |

\* cited by examiner

BEAM PROFILE COMPLEX REFLECTANCE SYSTEM AND METHOD FOR THIN FILM AND CRITICAL DIMENSION MEASUREMENTS

This application claims the benefit of U.S. Provisional Application No. 60/563,725, filed Apr. 19, 2004; and U.S. Provisional Application No. 60/568,215, filed May 3, 2004; and U.S. Provisional Application No. 60/610,896, filed Sep. 17, 2004; and U.S. Provisional Application No. 60/613,040, filed Sep. 25, 2004; and U.S. Provisional Application No. 60/624,865, filed Nov. 1, 2004; U.S. Provisional Application No. 60/640,182, filed Dec. 27, 2004; and U.S. Provisional Application No. 60/650,937, filed Feb. 7, 2005.

FIELD OF THE INVENTION

The present invention relates to reflectometry and ellipsometry, and more particularly to a method and system that combines reflectometry and ellipsometry for an improved technique in measuring thin film thickness, refractive indices, extinction coefficients and critical dimensions.

BACKGROUND OF THE INVENTION

Optical reflectometry and ellipsometry are commonly used to measure the thickness (t) and optical constants, refractive index (n) and extinction coefficient (k), of thin films deposited singly or in multi-layer stacks on substrates. Another major application is the measurement of critical dimensions (CD measurements), such as height, width, thickness, wall slope, etc, of fine geometric structures such as lines, trenches, vias, etc, in integrated circuits. For applications in semiconductor manufacturing, the requirements on precision, repeatability and system-to-system matching are becoming ever more demanding. Furthermore, the ever-decreasing geometries translate into ever-decreasing measurement areas, and thus the requirements for ever-smaller measurement spots. Examples of spectrometers and ellipsometers for thin film and CD measurements are U.S. Pat. Nos. 3,824,017, 4,293,224, 4,555,766, 5,867,276, 5,963,329 and 5,739,909, which are incorporated herein by reference. In addition, a thorough discussion of many prior art spectral ellipsometry systems can be found in the text by R. M. A. Azzam and N. M. Bashara entitled Ellipsometry and Polarized Light, North Holland Physics Publishing, 1988.

To address these application needs, current thin film and CD metrology systems used in the semiconductor industry typically employ both DUV-VIS (deep ultraviolet-visible) spectral reflectance at normal incidence together with off-axis rotating spectral ellipsometry in the range of 190-900 nm using focused optical beams. Some metrology systems, such as those manufactured by Therma-Wave, Inc. of Fremont, Calif., also include laser-based single wavelength beam profile reflectometry (BPR) and beam profile ellipsometry (BPE) technologies in addition to the more conventional spectral reflectometry and spectral ellipsometry technologies. Examples of BPR and BPE systems for thin film and CD measurements are U.S. Pat. Nos. 4,999,014, 5,042,951, 5,181,080, 5,412,473, 5,596,411, 6,678,046, 6,654,131, 6,813,034, 6,829,057 and 6,842,259, which are incorporated by reference.

Conventional laser-based BPR and BPE technologies have the advantages of better signal/noise ratios and smaller spot sizes, but at present are only single wavelength devices, and thus do not have the same capabilities as the spectral technologies. Thus these BPR and BPE methods are generally combined with conventional normal-incidence spectrometers and conventional off-axis spectral ellipsometers that employ rotating ellipsometric optical elements, such as polarizers, analyzers or compensators. In addition, conventional BPE measurements suffer from phase fluctuations arising from the environmentally sensitive birefringence of the high-NA focusing objective. Moreover, conventional BPR and BPE systems tend to be complex, and include many optical components and detector assemblies, thereby increasing system-to-system variances. Further, if BPR and BPE methods, as well as conventional spectroscopy and spectral ellipsometry methods, are used to analyze the same wafer, it is virtually impossible to focus these separate systems onto and analyze the same spot on the wafer, and this tends to result in increased noise and measurement error. Furthermore, phase fluctuations from the focusing objective, together with rotation artifacts of the compensator or analyzer, contribute to additional signal noise and measurement error in these systems.

There is a need for a spectroscopic approach that combines the advantages of spectral reflectometry, spectral ellipsometry and the laser-based BPR and BPE technologies while minimizing the disadvantages of these complex combination systems. A new spectroscopic BPR+BPE technology could perform all of the measurements of the different methods and would be a significant improvement over the current methods.

SUMMARY OF THE INVENTION

The present invention solves the aforementioned problems by providing a spectroscopic measurement device and method of measuring both the magnitude and phase of reflected light from the sample simultaneously over a wide range of angles of incidence and over multiple azimuthal angles The present invention is a device for measuring the complex reflectance of light reflected off of a sample surface, that includes means for generating a light beam with a known polarization state; means for focusing the light beam substantially normal onto the surface of the sample such that various rays within the focused light beam create a spread of angles of incidence $\theta$ with respect to the sample surface, wherein the focused light beam reflects off of the sample surface, means for producing a relative retardation in phase between parallel and perpendicular polarization states of the light beam, means for generating interference between the parallel and perpendicular polarization states of the reflected light beam, detector means positioned in the path of the reflected light beam having a two dimensional array of detector elements for receiving the reflected light beam and producing intensity signals in response thereto, wherein each of the detector elements corresponds to a unique angle of incidence $\theta$ and azimuthal angle $\phi$ of the reflected light beam, and a processor means for calculating magnitude and phase values for the reflected light beam by using the intensity signals corresponding to at least one incident angle $\theta$ and a plurality of azimuthal angles $\phi$ within the at least one incident angle $\theta$ sufficient to enable a meaningful Fourier analysis thereof, and for determining a physical characteristic of the sample based on the calculations.

In another aspect of the present invention, a method of measuring the complex reflectance of light reflected off of a sample surface includes generating a light beam with a known polarization state, focusing the light beam substantially normal onto the surface of the sample such that various rays within the focused light beam create a spread of angles of incidence θ with respect to the sample surface, wherein the focused light beam reflects off of the sample surface, producing a relative retardation in phase between parallel and perpendicular polarization states of the light beam, generating interference between the parallel and perpendicular polarization states of the reflected light beam, receiving the reflected light beam and producing intensity signals in response thereto using a two dimensional array of detector elements in a detector with each of the detector elements corresponding to a unique angle of incidence θ and azimuthal angle φ of the reflected light beam, calculating magnitude and phase values for the reflected light beam by using the intensity signals corresponding to at least one incident angle θ and a plurality of azimuthal angles φ within the at least one incident angle θ sufficient to enable a meaningful Fourier analysis thereof, and determining a physical characteristic of the sample based on the calculations.

Other objects and features of the present invention will become apparent by a review of the specification, claims and appended figure.

DETAILED DESCRIPTION OF THE PREFERRED EMBODIMENTS

Figure 1:
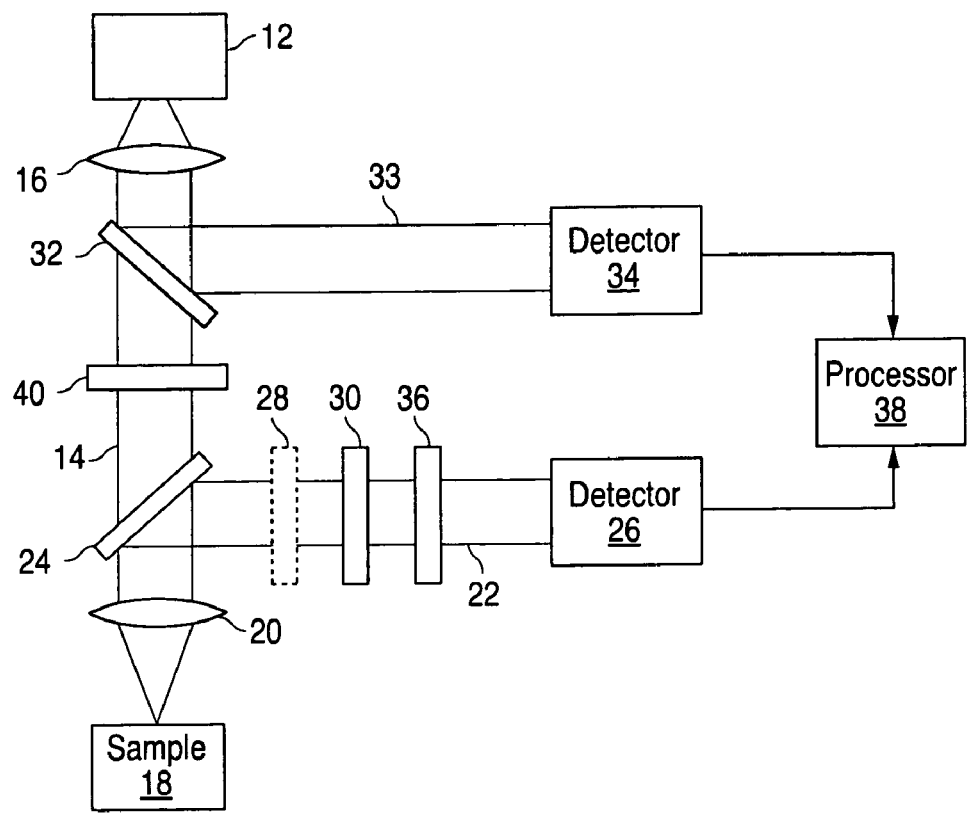
FIG. 1 is a plan view of the complex reflectance measuring device of the present invention.

The present invention is a new and improved method and apparatus for measuring the thickness and optical constants of thin films deposited on substrates and of critical dimensions of circuit structures. More specifically, the present invention measures the spectroscopic complex reflectance from a sample surface, where both the magnitude and phase of reflected light from the sample is obtained simultaneously over a wide range of angles of incidence and over all azimuthal angles, and at different wavelengths, by combining beam profile reflectometry (BPR) and beam profile ellipsometry (BPE) measurements into a single measurement device and method using a single 2-dimensional detector. Thus, the combination of BPR and BPE using multiple wavelengths can be referred to as a spectral BP2 technology, to emphasize that it is a two-dimensional beam profile technology.

The optical probe beam is directed normal to the sample surface and is tightly focused by means of a high numerical aperture (NA) lens. In one preferred embodiment, the probe beam wavelength is time-multiplexed by illuminating the sample sequentially with light beams of different wavelengths. In another preferred embodiment, the probe beam is from a white light source or a polychromatic source and the spectroscopic signal is obtained by use of a suitable color-coded detector system. The present invention need not use rotating optical elements, thereby eliminating a major source of measurement error and system-to-system variance.

The present invention improves the precision and repeatability of current optical metrology systems by employing a combined 2-dimensional BPR and BPE technique that is spectroscopic. The subject invention, the BP2 technology, combines both BPR and BPE in one detector subsystem, thereby decreasing system-to-system variances and enhancing system-to-system matching by the elimination of numerous optical components and multiple detector assemblies. Another advantage of the present invention is that both the reflectometry (BPR) measurement and the ellipsometry (BPE) measurement, which together measure the total complex reflectance, are performed at exactly the same spot on the wafer using the same incident light beam, with the two measurements using the same optical path and the same detector, thereby eliminating several significant sources of signal noise and measurement error. Another major advantage of the BP2 technology is that a much smaller measurement spot is available since the beam is focused normal to the sample. This is in contrast to a conventional off-axis ellipsometer that will typically produce a much larger illumination spot on the sample. The larger spot is the result of both the high angle of incidence of the off-axis beam, typically 65°, and the relatively low NA focusing lens that must be used for such a high angle of incidence. The smaller spot available with BP2 technology reduces the measurement area needed on the wafer, or alternatively reduces the time to make a measurement within the same size measurement area since the spectral intensity is greater in the normal incidence high NA BP2 technology. Also the present invention greatly improves the precision and repeatability of the BPE measurement by minimizing the effects of phase fluctuations from the focusing objective. In addition, the preferred embodiment does not use a rotating compensator or a rotating analyzer, thereby eliminating these major sources of signal noise and measurement error. Most significantly, the BP2 technology, when utilizing multiple wavelengths, can by itself perform all of the measurements currently being done by the four separate techniques, spectroscopic reflectometry, spectral ellipsometry, BPR and BPE, thereby greatly simplifying the measurement system, improving measurement precision, and minimizing sources of error and system-to-system variance.

As shown in FIG. 1, the BP2 measurement system 10 of the present invention includes a light source 12 generating a probe beam of light (radiation) 14 that is collimated by lens 16 and focused at normal incidence onto the sample 18 by a high NA objective lens 20. If the probe beam is from a laser, the high power density of the light beam 14 results in high signal/noise ratios and the beam is focused to about a one micron diameter spot (1/e points). However, because of the large spatial coherence of the laser beam, the effective measurement spot with a Gaussian laser beam of 1 micron is still 20-30 microns because of interference effects from the Gaussian tail. When the probe beam is an incoherent beam, the spectral intensity is lower and the focused spot larger, but the effective measurement spot can still be 20-30 microns because there is little interference from spatial coherence effects. It may be possible to use a laser as the light source and achieve even smaller measurement areas if one can reduce the spatial coherence. This is possible if the coherence of the laser beam is reduced, that is, if one makes the laser beam partially incoherent. There are various ways to decrease the coherence of a laser beam: 1) transmit the probe beam through a stationary or spinning ground glass or opal glass, 2) employ acoustic or ultrasonic vibration of the fiber carrying the laser beam, or 3) electronic modulation of the wavelength of a diode laser source. It should be noted that as the coherence of the laser beam is decreased, the nominal 1/e focused spot size will be increased at the same time as the edge effects from the Gaussian tails are reduced. Nevertheless, by employing partially incoherent laser beams, the measurement box size can be reduced to 10 microns or less, while maintaining a 1/e focused spot size of only a few microns.

For both coherent and incoherent beams, the incident light beam 14 is highly focused, and it contains rays at angles of incidence ranging from 0° to $\theta_{max}=\sin^{-1}(NA)$. Thus for a focusing lens with an NA of 0.90, $\theta_{max} \approx 64°$, and for an NA of 0.95, $\theta_{max} \approx 72°$. Light reflected by the sample constitutes a reflected probe beam 22 having information about the complex reflectance (magnitude and phase) generated by the sample for a large range of angles of incidence. This information can be accessed by analyzing the magnitude and the phase of all the rays comprising the reflected probe beam 22. This is done by directing the reflected beam 22 using a beam splitter 24 to a detector 26. Since there is a one-to-one correspondence between the angle of incidence of any ray and the radial position of the ray within the cross-sectional profile of the reflected beam 22 formed at the back focal or Fourier plane of the lens, BPR analysis provides information about the magnitudes of the S (polarization perpendicular to the plane of incidence) and P (polarization parallel to the plane of incidence) reflectances from the sample surface ($|R_S|$ and $|R_P|$), and a BPE analysis provides information about the phase difference between $R_S$ and $R_P$ as a function of the angle of incidence.

Preferably, the light source 12 will produce a light beam 14 that is either a white light beam or is composed of several different wavelengths. Light source 12 may be a Xe arc lamp, a combination of a Xe arc plus a deuterium arc lamp, or a tungsten lamp, all of which can provide light over a broad spectral range. Light source 12 may also include multiple narrow band light sources (e.g. lasers or LED devices) whose beams are incident on the sample either sequentially or simultaneously. It is preferable to cover as wide a spectral range as possible using suitable high NA focusing objective lens 20, which may be refractive, reflective or catadioptric.

In one preferred embodiment, the different light wavelengths are utilized sequentially in the incident probe beam, that is, the sample 18 is illuminated by one wavelength (or a very small band of wavelengths) of light at a time using a monochromator or suitable color filters. If the incident probe beam 14 is white light or multi-wavelength, then the reflected probe beam 22 can be analyzed in a sequentially spectroscopic fashion by use of optional narrow bandpass optical filters 28, or a monochromator, or simultaneously with a suitable color-coded detector system.

The incident beam 14 needs to have a known polarization state. For the purposes of this disclosure, it is assumed that polarization state is linear polarization. Linearly polarized light can be produced directly from the light source (e.g. a property of a laser source), or can be generated by using an optional linear polarizer element 40. Other polarization states can include circular polarization or other forms of elliptical polarization. However, linearly polarizing the incident beam 14 is preferred, because it greatly simplifies the equations (and thus the analysis) discussed below. A portion of the incident probe beam 14 can be split off using a beam splitter 32 to create a normalizing beam 33 directed to a power detector 34 to monitor the power of beam 14. The power detector 34 can be used to produce a normalizing signal for measuring, correcting and/or compensating for light power fluctuations.

The reflected beam 22 is transmitted through a waveplate, or compensator, such as a quarter-wave plate 30 oriented to retard one of the polarization states of the beam relative to the other polarization state. It is also possible to locate the compensator 30 in the incident probe beam 14. Prior to reaching the detector 26, the beam is passed through a linear analyzer 36 that is oriented such that it causes the two polarization states of the reflected probe beam 22 to interfere with each other. The detector 26 is a 2-dimsional array detector such as a CCD array or camera for measuring the optical power of the reflected probe beam 22 as a function of position within the reflected probe beam. Detector 26 includes a plurality of detector elements (pixels) each positioned to measure the intensity of a different cross-sectional segment of reflected probe beam 22 and produce an individual signal reflecting the measured intensity. Each detector element measures a unique and independent segment of the reflected beam, and each beam segment in turn corresponds to individual light rays incident on the sample at a distinct angle of incidence and azimuthal angle. The use of a sufficient number of the detector elements in the 2-dimensional array or CCD camera in the analysis provides information that eliminates the need for a rotating compensator or a rotating analyzer, thereby removing these major sources of signal noise and measurement error. Moreover, additional information can be gathered about the sample by using all or substantially all of the 2-dimensional array of detector elements illuminated by the reflected beam 22 (i.e. using detector elements to measure a substantial portion of the beam profile), as opposed to conventional ellipsometric devices that employ essentially only one angle of incidence and use a rotating compensator or analyzer, or prior BPE devices that only utilize detector elements oriented along two orthogonal axes with integration over a range of azimuthal angles, or in conjunction with a rotating compensator or analyzer.

A processor 38 is connected to the detectors 26 and 34 to collect the normalizing information measured by detector 34 (for probe beam 14) and the information measured by the pixels of the two dimensional array/camera 26 (for the reflected probe beam 22). The processor makes calculations according to the equations discussed below to determine physical characteristics (e.g. thickness, refractive index and extinction coefficient) of thin films deposited singly or in multi-layer stacks on a substrate of the sample 18, or of critical dimensions of circuit structures on the substrate of sample 18.

For the purposes of the following discussion, the polarization state of the probe beam 14 shall be assumed to be linear polarization. Leaving out for now any phase shifts arising from the birefringence of the objective lens 20, or other artifacts, the signal recorded at any given detector element of detector 26 (corresponding to the angles ($\theta;\phi$) where $\theta$ is the angle of incidence and $\phi$ the azimuthal angle as measured from the axis of the incident beam polarization—i.e. the axis of linear polarizer 40 if used) is also a function of the azimuthal angle $\omega$ of the axis of the compensator 30 and the azimuthal angle $\alpha$ of the analyzer 36 (also as measured from the axis of the incident beam polarization). For a common orientation of $\omega=0$, we have, $$S(\theta, \phi) = \frac{1}{8} I_i(r, \phi) |R_S(\theta)|^2 \left\{ \begin{array}{l} (\tan^2\psi(\theta) + 1)(2 + \cos 2\alpha) + 2\tan\psi(\theta)\cos\delta(\theta)\cos 2\alpha + \\ 2(\tan^2\psi(\theta) - 1)(1 + \cos 2\alpha)\cos 2\varphi + \\ 4\tan\psi(\theta)\sin\delta(\theta)\sin 2\alpha\sin 2\varphi + \\ (\tan^2\psi(\theta) + 1 - 2\tan\psi(\theta)\cos\delta(\theta))\cos 2\alpha\cos 4\varphi \end{array} \right\} \quad (1)$$

where $I_i(r,\phi)$ gives the incident probe beam profile intensity as a function of the distance from the center of the probe beam, $r=\sin\theta$, and of $\phi$ the azimuthal angle. The complex reflectances, $R_S(\theta)$ (polarization perpendicular to the plane of incidence) and $R_P(\theta)$ (polarization parallel to the plane of incidence) are given by the well known Fresnel reflection equations and are functions only of the angle of incidence $\theta$. These Fresnel equations are well known to those skilled in the art, and are not further described herein. The ellipsometric parameters tan $\psi$, which represents the ratio of the absolute magnitudes of the two complex reflectances, and $\delta$, which represents the relative phase difference between these two complex reflectances, are given by, $$\frac{R_P(\theta)}{R_S(\theta)} = \frac{|R_P(\theta)|}{|R_S(\theta)|}e^{i\delta(\theta)} = \tan\psi(\theta)e^{i\delta(\theta)} \quad (2)$$

From Eqn. (1), one can see that an analysis of the BP2 data set $S(\theta,\phi)$ will provide information about the two ellipsometric parameters tan $\psi$ and $\delta$ for the different angles of incidence $\theta$. The BP2 signal $S(\theta,\phi)$ in Eqn. (1) is periodic in both $2\phi$ and $4\phi$, and thus can be analyzed in Fourier components of $\phi$. It can be readily shown that a Fourier analysis of the BP2 signal is equivalent to a Fourier analysis to obtain the harmonic terms in a conventional off-axis ellipsometer that employs a rotating polarizer, analyzer or compensator.

When $\alpha=\pi/4$, the signal $S(\theta,\phi)$ becomes, $$S(\theta,\phi) = \frac{1}{4}I_r(r,\phi)|R_S(\theta)|^2 \left\{ \begin{array}{l} \tan^2\psi(\theta) + 1 + [\tan^2\psi(\theta) - 1]\cos 2\phi + \\ 2\tan\psi(\theta)\sin\delta(\theta)\sin 2\phi \end{array} \right\} \quad (3)$$

Equation (3) has two Fourier components, one in cos $2\phi$ and the other in sin $2\phi$. We also see that only sin $\delta(\theta)$ is present. A similar situation holds for $\alpha=0$. Once again we have two Fourier components, but now only cos $\delta(\theta)$ is present. This situation is analogous to the case of a conventional off-axis ellipsometer with a rotating polarizer or a rotating analyzer. In many cases such a situation is insufficient for complete sample analysis, since a signal with only sin $\delta(\theta)$ will be insensitive to changes in the ellipsometric phase $\delta$ when $\delta$ is large, while a signal with only cos $\delta(\theta)$ will be insensitive to $\delta$ when $\delta$ is small. Ideally, one would like the signal $S(\theta,\phi)$ to contain terms in both sin $\delta(\theta)$ and cos $\delta(\theta)$. We can see that this is possible when $\alpha=\pi/8$, where the signal becomes, $$S(\theta,\phi) = \frac{1}{16}I_i(r,\phi)|R_S(\theta)|^2 \left\{ \begin{array}{l} (4+\sqrt{2})(\tan^2\psi(\theta)+1) + 2\sqrt{2}\tan\psi(\theta)\cos\delta(\theta) + \\ (4+\sqrt{2})(\tan^2\psi(\theta)-1)\cos 2\varphi + \\ 4\sqrt{2}\tan\psi(\theta)\sin\delta(\theta)\sin 2\varphi + \\ \sqrt{2}(\tan^2\psi(\theta)+1-2\tan\psi(\theta)\cos\delta(\theta))\cos 4\varphi \end{array} \right\} \quad (4)$$

By comparing Eqn. (4) with Eqn. (3), we see that the magnitude of the sin $\delta$ Fourier term is reduced by only 30% compared to the $\alpha=\pi/4$ case, and the cos $\delta$ Fourier term is ½ the magnitude of the sin $\delta$ term. Thus, setting $\alpha=\pi/8$ (22.5°) is a good compromise. Alternatively, one could selectively rotate the analyzer 36 to $\alpha=\pi/4$ when one wants to maximize the sin $\delta$ term and then to $\alpha=0$ or $\pi/2$ when one wants to maximize the cos $\delta$ term. However, since the magnitudes of these two terms only decrease by 30% when going from the optimal $\alpha$ settings to a fixed $\alpha$ setting of $\pi/8$, the fixed setting may be preferable, since even a set rotation may introduce additional measurement errors and system-to-system variances. Setting the angle $\alpha$ of the analyzer 36 to $\pi/8$ thus provides information about both cos $\delta$ and sin $\delta$ thereby significantly improving the ability to measure small changes in the phase $\delta(\theta)$ irrespective of its actual magnitude. This, in turn, enhances the capability of the BP2 technology to perform both thin film and critical dimension (CD) measurements.

It should be noted that for some applications it may be desirable to alternate between the two analyzer angles $\pi/4$ and 0 (or $\pi/2$) to separately maximize the sin $\delta$ and cos $\delta$ terms, and for other applications it may be advantageous to make measurements at more than two angles. This can be done by keeping the compensator angle $\omega$ fixed and using two or more analyzer angles $\alpha$, or alternately keeping $\alpha$ fixed and using two or more compensator angles $\omega$. The most generalized way of accomplishing this is to actually fully rotate either the analyzer or the compensator. The Fourier coefficients would then be dependent on both the azimuthal angle $\phi$ and on either the analyzer angle $\alpha$ or the compensator angle $\omega$. One can also rotate the polarizer angle while keeping the angles of the compensator and analyzer fixed. One can even rotate two of the three angles. Rotation in BP2 results in a much more complex situation than that of the basic BP2 configuration described above (using fixed angles), but this modification may be advantageous for certain applications.

We can see that, in addition to having terms in both sin $\delta(\theta)$ and cos $\delta(\theta)$, Eqn. (4) also has three Fourier components, sin $2\phi$, cos $2\phi$ and cos $4\phi$. This situation is analogous to the case of a conventional off-axis ellipsometer with a rotating compensator. Thus another advantage of the $\alpha=\pi/8$ case is the presence of 3 Fourier components which provides more independent information than the case of only 2 Fourier components. This assists in materials analysis and in dealing with system artifacts.

There is also a configuration where we can have the maximum number of Fourier components, 4, and that is where we set the compensator angle, $\omega=\pi/8$, and the analyzer angle, $\alpha=0$. With this configuration, the BP2 signal becomes, $$S(\theta,\phi) = \frac{1}{16}I_i(r,\phi)|R_S(\theta)|^2 \left\{ \begin{array}{l} 5(\tan^2\psi(\theta)+1) + 2\tan\psi(\theta)\cos\delta(\theta) + 6(\tan^2\psi(\theta)-1)\cos 2\varphi + \\ 2(\tan^2\psi(\theta)-1-2\sqrt{2}\tan\psi(\theta)\sin\delta(\theta))\sin 2\varphi + \\ (\tan^2\psi(\theta)+1-2\tan\psi(\theta)\cos\delta(\theta))\cos 4\varphi + \\ (\tan^2\psi(\theta)+1-2\tan\psi(\theta)\cos\delta(\theta))\sin 4\varphi \end{array} \right\} \quad (5)$$

From Eqn. (5), it can be seen that the configuration $\omega=\pi/8$ and $\alpha=0$ gives all 4 possible Fourier components, cos $2\phi$, sin $2\phi$, cos $4\phi$ and sin $4\phi$, thereby providing the most information.

Although Equations (1), (3), (4) and (5) have been obtained for certain values of the compensator angle $\omega$ and analyzer angle $\alpha$, similar expressions and conclusions can be derived using other equivalent angles. Also, similar expressions and conclusions can be derived for the case where the compensator is in the incident path.

For the general case of Eqn. (1), $S(\theta,\phi)$ is periodic in both $2\phi$ and $4\phi$. One can also show that the pure magnitude (BPR) signals will occur at $\phi=0$ and $\pi/2$ for any angle $\alpha$. At angle $\phi=0°$:

$$S(\theta,0)=\tfrac{1}{2}I_i(r,\theta)|R_P(\theta)|^2(1+\cos 2\alpha) \qquad (6)$$

and at $\phi=\pi/2$:

$$S(\theta,\pi/2)=\tfrac{1}{2}I_i(r,\theta)|R_S(\theta)|^2(1+\cos 2\alpha). \qquad (7)$$

Thus the BP2 signal $S(\theta,\phi)$ contains both magnitude (BPR) and phase (BPE) information and therefore provides a full description of both the S and P complex reflectances from the sample surface. It should be noted that this complex reflectance system is not simply an ellipsometer but is actually an integrated combination of an ellipsometer measuring magnitude and phase ($\phi\neq 0$, $\pi/2$) and a reflectometer measuring just magnitude ($\phi=0$, $\pi/2$).

By using a calibration sample with a precisely known thickness of a known film, such as $SiO_2$ on Si, one can use the above expressions for the BP2 signal $S(\theta,\phi)$ to map out all of the detector elements of the 2-dimensional detector array, such that each detector element has a known $(\theta,\phi)$ designation. One can then analyze an unknown sample to obtain $|R_S(\theta)|$, $|R_P(\theta)|=|R_S(\theta)|\tan\psi(\theta)$, and $\delta(\theta)$ as a function of the incident angle $\theta$, using appropriate least-squares fitting algorithms and Fourier analysis on the set of $S(\theta,\phi)$ data. From $|R_S(\theta)|$, $|R_P(\theta)|$ and $\delta(\theta)$ one can then obtain the complex reflectances $R_S(\theta)$ and $R_P(\theta)$. Then, using the Fresnel equations, one can obtain the thickness t and optical constants n and k of the unknown film or films, or, with the additional help of diffraction theory, one can obtain the critical dimensions of a circuit structure.

The measurement results will have high precision and repeatability because the data set $S(\theta,\phi)$ is much larger than the number of unknown variables, even for a sample stack consisting of several films, thereby ensuring a robust data fit. The fitting process can be repeated for each of the different wavelengths. This will enhance the precision of the thickness measurements, and provide spectral information on the optical constants n and k, thereby removing ambiguities when analyzing multi-layer film stacks or complex films.

It should be noted that the $|R_S(\theta)|$ and $|R_P(\theta)|$ measurements are BPR measurements while the $\delta(\theta)$ measurements are BPE measurements. Thus the present invention, the BP2 technology, by providing an analysis of both magnitude and phase for the full 2-dimensional beam profile, is in fact a combined BPR+BPE technology which uses a single detector system with no rotating optical components.

As noted above, the present invention also improves the precision and repeatability of the BPE measurement by minimizing the effects of phase fluctuations from the focusing objective lens 20. This is a result of the fact that the phase shift due to the birefringence of the focusing objective lens 20 is generally not dependent on the incident angle, $\theta$, and will, in general, have a symmetry dependence on $\phi$ that will be different from that of $S(\theta,\phi)$. This then provides an opportunity to separate out the sample signal from the objective birefringence signal, for example, by performing a Fourier analysis of the $S(\theta,\phi)$ data set to isolate the terms that are periodic in $2\phi$ and $4\phi$. Note again that such a Fourier analysis is similar to obtaining the harmonic terms from a rotating compensator (polarizer or analyzer) system.

An additional advantage of the present invention is that one does not need a separate full power detector for the reflected beam 22. A full power measurement helps to provide increased precision for measurements of very thin films. In the present invention, this full power measurement is performed by the same 2-dimensional detector array 26 by simply adding together the signals from all of the detector elements. Note that summing over all azimuthal angles removes all phase information, and one is left with only reflectance magnitude information, or normal-incidence reflectivity.

Another major advantage of the BP2 technology is that a much smaller measurement spot is available since the beam is focused normal to the sample. This is in contrast to a conventional off-axis ellipsometer that will typically produce a much larger illumination spot on the sample. The larger spot is the result of both the high angle of incidence of the off-axis beam, typically 65°, and the relatively low NA focusing lens that must be used with such a high angle of incidence. The smaller spot available with BP2 technology reduces the measurement area needed on the wafer, or alternatively reduces the time to make a measurement within the same size measurement area since the spectral intensity is greater in the normal incidence high NA BP2 technology.

Although this spectral BP2 technology is quite powerful for thin film and CD measurements, it may be useful, for certain applications, to combine the BP2 technology with a conventional DUV-VIS (190-840 nm) spectrometer that can be used in conjunction with the system 10 described above. The spectrometer measures the normal-incidence reflectivity as a function of wavelength. The spectral information is usually obtained by using a dispersing element such as a prism or a spectral grating to disperse the reflected beam across a linear detector array. This will provide measurement of the magnitude of the complex reflectance down to 190 nm or even lower. However, the spectrometer cannot provide phase measurements. It is therefore desirable to operate the BP2 technology as far into the UV as possible. This will require the use of DUV light sources and suitable high-NA reflective or catadioptric lenses. If one can extend the BP2 technology into the DUV, it may be possible to eliminate the use of a DUV-VIS spectrometer altogether, since the BP2 detector can, in principle, provide the same reflectivity information that a spectrometer provides. By simply summing all of the pixel information in the 2-D detector, one obtains the magnitude of the normal incidence reflectance. In addition, the effective NA of the reflectivity measurement, NA(eff), is easily controlled by setting the pixel summation from $\theta=0°$ to the desired maximum angle of incidence set by $\theta=\sin^{-1}[NA(eff)]$. A fully spectroscopic BP2 system thus can provide all of the measurements obtained from all 4 currently used techniques, a rotating spectral ellipsometer, a normal-incidence spectrometer and conventional laser-based BPR and BPE systems. This represents a major simplification of the measurement system.

In addition, some applications may also benefit by combining the BP2 technology with a high-precision off-axis laser ellipsometer for measurements on ultra-thin films. Such a system can include a laser producing a beam incident on the sample at high angle of incidence, typically 65°, that is not as tightly focused (typically around 10 microns). This high-precision laser ellipsometer is useful for ultra-thin films, such as gate films. Single wavelength ellipsometer systems are adequate if the film is a simple single layer. However, new gate films are becoming more complex and may consist of more than one layer. With the present invention, if different laser wavelengths are used in the spectral BP2 technology these same lasers also can be used in the laser ellipsometer as well. This will make the laser ellipsometric system spectroscopic and thus greatly enhance its ability to measure the more complex gate films.

One preferred embodiment of the present invention uses time-multiplexing of wavelengths. However, simultaneous wavelength illumination and analysis can reduce the total measurement time. Should it be desired, one can modify the apparatus described above to permit simultaneous illumination by all desired wavelengths and simultaneous detection of the beam profiles at each wavelength. There are at least two ways to accomplish simultaneous wavelength illumination and detection, both using either multiple narrow band light sources multiplexed together or a single polychromatic light source. The first way includes using a single color-coded 2-dimensional detector 26 that can simultaneously measure more than one wavelength. A common version of such a color-coded detector is the conventional color CCD camera which has an interleaved pattern of RGB pixels that are coated to pass either red (R), green (G) or blue (B) colors. Such an RGB detector would work well for spectral BP2 applications, since the variations in both the incidence and azimuthal angles between adjacent R, G and B pixels would be very small. For more precise measurements, one can also obtain separate $(\theta,\phi)$ maps for the detector at the different wavelengths. The RGB 2-dimensional detectors are readily available. An RGB 2D detector, or camera, is limited to three colors, red, green and blue. However, it is possible to employ appropriate optical coatings on the individual pixels, so that one can have several interleaved color codes (including custom selected colors), covering a number of different wavelengths (e.g. more than three if needed), including the ultraviolet. Such a multi-color 2-dimensional detector or camera would find many useful applications in spectroscopic imaging and measurements.

The second way to accomplish simultaneous wavelength illumination and detection is the addition of a high-dispersion grating or prism, or a separation of wavelengths by use of narrow-band filters and reflectors, after the reflected beam has passed through the analyzer. Suitable beam steering devices (e.g. beam splitters) would direct each primary wavelength or wavelength band to separate 2-dimensional detectors (i.e. entailing a separate 2-dimensional detector for each wavelength component in order to perform the separate beam profile analyses simultaneously). Although such an arrangement will decrease the total measurement time, it should be appreciated that the increase in optical components and detector assemblies will introduce additional noise and system-to-system variance sources. As such, a single color-coded 2-dimensional detector is preferable for simultaneous wavelength illumination and detection.

Another way to minimize the cost and complexity of separate multiple detectors would be to configure these separate 2-dimensional detectors as a customized single linear array of individual small 2-dimensional detectors, with these 2D detectors arranged in a linear array along the wavelength dispersion direction. Thus each 2D detector is recording the signal at a different wavelength. This linear array of 2D detectors is the analog of a linear array of single detectors, but where each single detector is replaced by a 2D detector. Since there would be up to 8 or 16 such 2D detectors arranged along the linear array, fairly small 2D detectors should be used, such as 128×128 pixel detectors. In addition, since each 2D detector extends as far along the wavelength dispersion direction as it does normal to this direction, appropriate narrow-band spectral filters should be placed in front of each 2D detector to prevent interference from adjacent wavelengths.

It should be noted that the new and improved method and apparatus for measuring the thickness and optical constants of thin films deposited on substrates described above can also be applied to the measurement of critical dimensions (CD measurements), such as height, width, thickness, wall slope, etc, of fine geometric structures such as lines, trenches, vias, etc, in integrated circuits. It is known that CD measurements can be performed on gratings and other arrays of these fine geometric structures by analyzing the far field diffraction effects on the signals detected in conventional spectroscopic reflectometers and ellipsometers. Similar diffraction effects will also be present in the 2-dimensional beam profile signals of the spectral BP2 method and apparatus disclosed above.

There are numerous advantages to performing CD measurements with the present invention. First, a smaller measurement spot is available since the beam is focused normal to the sample. This is in contrast to a conventional off-axis ellipsometer that will typically produce a much larger illumination spot on the sample. The larger spot is the result of both the high angle of incidence of the off-axis beam, typically 65°, and the relatively low NA focusing lens that must be used for such a high angle of incidence. The smaller spot available with BP2 technology reduces the measurement area needed on the wafer, or alternatively reduces the time to make a measurement within the same size measurement area since the spectral intensity is greater in the normal incidence high NA BP2 technology. Secondly, considerably more diffraction information is available in the 2-dimensional beam profile analysis (i.e. using a 2-dimensional array of detector elements to measure a substantial portion of the reflected beam profile), since in addition to the complex reflectance field, it provides simultaneous information about the complex diffraction field (both magnitude and phase) for all angles of incidence, $\theta$, from 0° to $\sin^{-1}(NA)$. Third, one also has simultaneous measurements for all azimuthal angles $\phi$ including both TE and TM modes, where the polarization is perpendicular and parallel to the longitudinal axis of the structure respectively. Thus one does not need to rotate the wafer. In addition, several major sources of signal noise and measurement error are eliminated since the BP2 method disclosed above obtains all of this information about the complex diffraction field from exactly the same measurement spot on the wafer and uses only one optical path and one detector.

Another major advantage of the present invention is that when using laser beams, the small spot size of the focused laser beam (approximately 1 micron) makes it possible to perform CD measurements on a single isolated feature. For example, a single line only 100 nm wide will still interact with about 10% of the focused beam thereby providing a fairly strong diffraction signal. The ability to measure single features with good signal/noise is a unique advantage of the BP2 technique of the present invention, since this is very difficult with conventional reflectance and ellipsometric techniques. This capability may be very important to the industry by removing the need to produce the special measurement gratings and arrays now in use, thus reducing production costs.

As discussed above for thin film measurements, the CD measurements would also be performed in spectroscopic fashion to provide more information and remove ambiguities in the analysis of the data.

Simpler, more specialized metrology systems, known as integrated systems, are now commonly used in process fabrication tools to monitor and control processes such as film deposition, etch, chemical-mechanical polishing and photoresist coating and stripping. These metrology systems are an integral component of the wafer processing tools. Key requirements of integrated systems are that they be small, fast and inexpensive. The subject invention is ideally suited for such an application. Because the number of unknown variables to be measured in a process control application is usually quite limited, the BP2 technology will be sufficient by itself for most applications, since both the magnitude and phase of the complex reflectance will be obtained for a wide range of angles of incidence. Furthermore, most applications would probably require only one or a few wavelengths. Such a system should prove sufficient for the majority of thin film and CD applications required in an integrated metrology system. More demanding integrated metrology applications might require the addition of a DUV-VIS spectrometer to be used together with the BP2 system and method of the present invention or the use of a fully spectroscopic BP2 system such as described above.

It should be noted that in order to generate meaningful results from the above described apparatus and method, the number of detector elements in detector 26 must be sufficient to enable a meaningful Fourier analysis. Therefore, for the purposes of this disclosure, a meaningful Fourier analysis is one that can take the data from the individual detector elements and obtain Fourier terms relative to the azimuthal angle $\phi$ and multiples of $\phi$, up to at least $2\phi$. Such an analysis can be done for each angle of incidence $\theta$ (i.e. multiple $\phi$'s along the concentric ring of detector elements representing a particular $\theta$). Although one does not require more than one $\theta$ to perform a single Fourier analysis, one does require a multiplicity of azimuthal angles $\phi$. For example, one would require at least 8 appropriately spaced values of $\phi$ to obtain a reliable $2\phi$ Fourier component, even with perfect data (i.e. no noise). In the presence of noise, the number of azimuthal angles needed for a reliable results rises. Similarly, to obtain reliable $4\phi$ Fourier components, one requires more than 16 appropriately spaced values of $\phi$. Thus, it can be generally said that detector 26 should have more than 8 equally spaced $\phi$'s (i.e. more than 8 equally spaced detector elements) for each $\theta$. In general, it is desirable to have as many $\phi$'s as possible covering the entire $2\pi$ range of $\phi$ to perform a meaningful Fourier analysis. It is also desirable to have as many $\theta$'s as possible so as to obtain reliable values for the ellipsometric parameters.

It is to be understood that the present invention is not limited to the embodiment(s) described above and illustrated herein, but encompasses any and all variations falling within the scope of the appended claims. For example, materials, processes and numerical examples described above are exemplary only, and should not be deemed to limit the claims. Further, as is apparent from the claims and specification, not all method steps need be performed in the exact order illustrated or claimed, but rather in any order that allows the proper light beam formation, sample interaction, and reflected beam detection of the present invention.

What is claimed is:

1. A device for measuring the complex reflectance of light reflected off of a sample surface, comprising:
   means for generating a light beam with a known polarization state;
   means for focusing the light beam substantially normal onto the surface of the sample such that various rays within the focused light beam create a spread of angles of incidence $\theta$ with respect to the sample surface, wherein the focused light beam reflects off of the sample surface;
   means for producing a relative retardation in phase between parallel and perpendicular polarization states of the light beam;
   means for generating interference between the parallel and perpendicular polarization states of the reflected light beam;
   detector means positioned in the path of the reflected light beam having a two dimensional array of detector elements for receiving the reflected light beam and producing intensity signals in response thereto, wherein each of the detector elements corresponds to a unique angle of incidence $\theta$ and azimuthal angle $\phi$ of the reflected light beam; and
   a processor means for calculating magnitude and phase values for the reflected light beam by using the intensity signals corresponding to at least one incident angle $\theta$ and a plurality of azimuthal angles $\phi$ within the at least one incident angle $\theta$ sufficient to enable a meaningful Fourier analysis thereof, and for determining a physical characteristic of the sample based on the calculations;
   wherein the retardation producing means and the interference generating means are stationary and oriented such that the signals from the detector have a first Fourier component that is dependent on azimuthal angle $2\phi$ and a second Fourier component independent of the first Fourier component that is dependent on azimuthal angle $4\phi$.

2. The device of claim 1, wherein the light beam includes at least one narrow band wavelength of light.

3. The device of claim 1, wherein the light beam includes polychromatic light.

4. The device of claim 3, wherein the light beam generating means comprises a plurality of narrow band lasers for producing a plurality of different wavelengths of light.

5. The device of claim 3, wherein the light beam generating means comprises a plurality of light emitting diodes for producing a plurality of different wavelengths of light.

6. The device of claim 3, wherein the light beam includes incoherent broadband light.

7. The device of claim 1, wherein the light beam generating means produces the light beam having coherent light, and the device further includes an element in the path of the light beam that renders the light in the light beam partially or substantially spatially incoherent.

8. The device of claim 1, wherein the known polarization state is linear polarization.

9. The device of claim 8, further comprising:
   a linear polarizing element disposed in the path of the light beam for generating the linear known polarization state.

10. The device of claim 8, wherein the retardation producing means is a compensator.

11. The device of claim 10, wherein the interference generating means is a polarizing analyzer.

12. The device of claim 10, wherein the compensator is positioned in the path of the light beam between the light beam generating means and the sample.

13. The device of claim 10, wherein the compensator is positioned in the path of the reflected light beam between the sample and the interference generating means.

14. The device of claim 1, wherein the retardation producing means and the interference generating means are oriented with the light beam such that the detector intensity signals have components dependent on both ellipsometric parameters $\tan\psi$ and $\delta$ of the sample.

15. The device of claim 1, wherein the detector means provides signals at more than 8 independent values of the azimuthal angle $\phi$ for each of a plurality of the angles of incidence $\theta$.

16. The device of claim 15, wherein the more than 8 independent values of the azimuthal angle $\phi$ are equally spaced from each other for each of the plurality of the angles of incidence $\theta$.

17. The device of claim 1, wherein the interference generating means is oriented at an angle of $\pi/8$ or a 45 degree multiple thereof relative to the polarization state.

18. The device of claim 11, wherein the polarizing analyzer is oriented at an angle of $\pi/8$ or a 45 degree multiple thereof relative to the linear polarization state.

19. The device of claim 1, wherein the light beam generating means sequentially produces light in the light beam of different wavelengths.

20. The device of claim 3, further comprising:
means for selecting different wavelengths of light from the reflected light beam such that the detector is sequentially illuminated with different wavelengths of light.

21. The device of claim 3, wherein the detector includes a plurality of detectors, and the device further comprises:
means for simultaneously illuminating different one's of the plurality of detectors with different wavelengths of light from the reflected light beam.

22. The device of claim 3, wherein the detector includes a linear array of 2-dimensional detectors, and the device further comprises:
means for spectrally dispersing the reflected light beam onto the linear array of 2-dimensional detectors.

23. The device of claim 22, further comprising:
a plurality of narrow band color filters disposed in front of the 2-dimensional detectors.

24. The device of claim 1, wherein the light beam generating means generates first and second wavelengths of light in the light beam, and wherein the detector elements include first elements thereof sensitive to the first wavelength and not the second wavelength that are interleaved among second elements thereof sensitive to the second wavelength and not the first wavelength.

25. The device of claim 1, wherein the light beam generating means generates at least first, second and third different wavelengths of light in the light beam, and wherein the detector elements include first elements thereof sensitive to the first wavelength and not the second and third wavelengths, second elements thereof sensitive to the second wavelength and not the first and third wavelengths, and third elements thereof sensitive to the third wavelength and not the first and second wavelengths, and wherein the first, second and third elements of the detector elements are interleaved among each other.

26. The device of claim 1, wherein the physical characteristic includes at least one of a thickness, a refractive index, and an extinction coefficient of a thin film formed on a substrate of the sample.

27. The device of claim 1, wherein the physical characteristic includes at least one of the critical dimensions of an array of circuit structures or grating formed on a substrate of the sample.

28. The device of claim 1, wherein the physical characteristic includes at least one of the critical dimensions of a single isolated circuit structure formed on a substrate of the sample.

29. The device of claim 1, further comprising:
beam splitting means for creating a normalizing light beam from the light beam; and
second detector means for measuring an intensity of the normalizing light beam.

30. The device of claim 1, wherein the processor means obtains normal-incidence reflectivity measurements by summing the intensity signals from the detector elements corresponding to all the azimuthal angles $\phi$ and all incidence angles $\theta$.

31. The device of claim 1, wherein the processor means obtains normal-incidence reflectivity measurements at an effective numerical aperture of NA(eff) by summing the intensity signals from the detector elements corresponding to all the azimuthal angles $\phi$ and to the incidence angles $\theta$ ranging from zero degrees to $\sin^{-1}[NA(eff)]$.

32. The device of claim 1, further comprising the addition of a conventional normal incidence spectrometer to obtain an independent measure of sample reflectivity as a function of wavelength.

33. The device of claim 1, further comprising the addition of a laser-based off-axis rotating ellipsometer to obtain an independent measure of the parameters of the sample.

34. The device of claim 1, wherein the device is integrated into a processing tool for implementing fabrication processing on the sample, and wherein the device directly monitors and controls the fabrication processing being performed by the process tool.

35. A method of measuring the complex reflectance of light reflected off of a sample surface, comprising:
generating a light beam with a known polarization state;
focusing the light beam substantially normal onto the surface of the sample such that various rays within the focused light beam create a spread of angles of incidence $\theta$ with respect to the sample surface, wherein the focused light beam reflects off of the sample surface;
producing a relative retardation in phase between parallel and perpendicular polarization states of the light beam;
generating interference between the parallel and perpendicular polarization states of the reflected light beam;
receiving the reflected light beam and producing intensity signals in response thereto using a two dimensional array of detector elements in a detector with each of the detector elements corresponding to a unique angle of incidence $\theta$ and azimuthal angle $\phi$ of the reflected light beam;
calculating magnitude and phase values for the reflected light beam by using the intensity signals corresponding to at least one incident angle $\theta$ and a plurality of azimuthal angles $\theta$ within the at least one incident angle $\theta$ sufficient to enable a meaningful Fourier analysis thereof; and
determining a physical characteristic of the sample based on the calculations;

wherein the producing of the retardation and the generating of the interference are performed using stationary elements that are oriented such that the signals from the detector have a first Fourier component that is dependent on azimuthal angle 2θ and a second Fourier component independent of the first Fourier component that is dependent on azimuthal angle 4θ.

36. The method of claim 35, wherein the light beam includes at least one narrow band wavelength of light.

37. The method of claim 35, wherein the light beam includes polychromatic light.

38. The method of claim 37, wherein the generating of the light beam is performed by a plurality of narrow band lasers that produce a plurality of different wavelengths of light.

39. The method of claim 37, wherein the generating of the light beam is performed by a plurality of light emitting diodes that produce a plurality of different wavelengths of light.

40. The method of claim 37, wherein the light beam includes incoherent broadband light.

41. The method of claim 35, wherein the light beam is generated as coherent light, the method further comprising:
rendering the coherent light beam partially or substantially spatially incoherent.

42. The method of claim 35, wherein the known polarization state is linear polarization.

43. The method of claim 35, wherein the generating of retardation is performed before the focusing of the light beam onto the sample surface.

44. The method of claim 35, wherein the generating of retardation is performed after the reflection of the light beam from the sample surface.

45. The method of claim 35, wherein the producing of the retardation and the interference are performed such that the detector intensity signals have components dependent on both ellipsometric parameters tanψ and δ of the sample.

46. The method of claim 35, wherein the detector provides signals at more than 8 independent values of the azimuthal angle φ for at least one angle of incidence θ.

47. The method of claim 46, wherein the more than 8 independent values of the azimuthal angle φ are equally spaced from each other.

48. The method of claim 35, wherein the stationary elements comprise a polarizing analyzer that is oriented at an angle of π/8 or a 45 degree multiple thereof relative to the known polarization state.

49. The method of claim 46, wherein the stationary elements comprise a polarizing analyzer that is oriented at an angle of π/8 or a 45 degree multiple thereof relative to the linear polarization.

50. The method of claim 35, wherein the generating of the light beam includes sequentially producing light in the light beam of different wavelengths.

51. The method of claim 37, further comprising:
selecting different wavelengths of light from the reflected light beam such that the detector is sequentially illuminated with different wavelengths of light.

52. The method of claim 37, wherein the detector includes a plurality of detectors, further comprising:
simultaneously illuminating different one's of the plurality of detectors with different wavelengths of light from the reflected light beam.

53. The method of claim 37, wherein the detector includes a linear array of 2-dimensional detectors, further comprising:
spectrally dispersing the reflected light beam onto the linear array of 2-dimensional detectors.

54. The method of claim 35, wherein the light beam includes first and second wavelengths of light, and wherein the detector elements include first elements thereof sensitive to the first wavelength and not the second wavelength that are interleaved among second elements thereof sensitive to the second wavelength and not the first wavelength.

55. The method of claim 35, wherein the light beam includes at least first, second and third different wavelengths of light, and wherein the detector elements include first elements thereof sensitive to the first wavelength and not the second and third wavelengths, second elements thereof sensitive to the second wavelength and not the first and third wavelengths, and third elements thereof sensitive to the third wavelength and not the first and second wavelengths, and wherein the first, second and third elements of the detector elements are interleaved among each other.

56. The method of claim 35, wherein the physical characteristic includes at least one of a thickness, a refractive index, and an extinction coefficient of a thin film formed on a substrate of the sample.

57. The method of claim 35, wherein the physical characteristic includes at least one of the critical dimensions of an array of circuit structures or grating formed on a substrate of the sample.

58. The method of claim 35, wherein the physical characteristic includes at least one of the critical dimensions of a single isolated circuit structure formed on a substrate of the sample.

59. The method of claim 35, further comprising:
creating a normalizing light beam from the light beam; and
measuring an intensity of the normalizing light beam.

60. The method of claim 35, further comprising:
summing the intensity signals from the detector elements corresponding to all the azimuthal angles φ and all incidence angles θ.

61. The method of claim 35, further comprising:
summing the intensity signals from the detector elements corresponding to all the azimuthal angles φ and to the incidence angles θ ranging from zero degrees to $\sin^{-1}$[NA(eff)].

* * * * *